United States Patent [19]

Jarkewicz

[11] Patent Number: 4,585,008
[45] Date of Patent: Apr. 29, 1986

[54] REAL TIME CARDIAC RADIONUCLIDE IMAGING

[75] Inventor: Gary G. Jarkewicz, Willoughby, Ohio

[73] Assignee: Technicare Corporation, Solon, Ohio

[21] Appl. No.: 427,075

[22] Filed: Sep. 29, 1982

[51] Int. Cl.$^4$ .............................................. A61B 6/00
[52] U.S. Cl. .................................... 128/654; 128/659
[58] Field of Search ........................ 128/653, 654, 659

[56] References Cited

U.S. PATENT DOCUMENTS

| | | | |
|---|---|---|---|
| 4,245,647 | 1/1981 | Randall | 128/659 |
| 4,336,820 | 1/1983 | Heyda et al. | 128/659 |
| 4,444,196 | 4/1984 | Stein | 128/654 |

Primary Examiner—Kyle L. Howell
Assistant Examiner—John C. Hanley
Attorney, Agent, or Firm—Audley A. Ciamporcero, Jr.; Michael A. Kaufman

[57] ABSTRACT

Real time acquisition of cardiac or other gated cyclical data using a scintillation camera with image formulation utilizing only such data that satisfied a preselected time frame for each cycle. The technique provides real time processing of gated data without the need for specialized hardware equipment or for post processing of the data. Unwanted information corresponding to cycles falling outside a preselected time frame are deleted in real time and hence do not contribute to the cumulative cardiac image.

4 Claims, 7 Drawing Figures

REAL TIME CARDIAC RADIONUCLIDE IMAGING

TECHNICAL FIELD OF THE INVENTION

This invention relates to cardiac radionuclide imaging and in particular to real time cardiac data acquisition using a disk subsystem.

BACKGROUND ART

Although nuclear medicine was traditionally limited to studies of organs exhibiting little internal motion, advances in the state of the art have made the collection of data related to heart function a common procedure today. Nonetheless, irregularities in a patient's heart rate (even where such patient is relatively immobile, as is the case during a nuclear study) makes the real time acquisition of reliable cardiac data a difficulty.

In conventional nuclear imaging of relatively immobile body parts, information accumulates at a relatively slow rate so the study is simply continued until a sufficient amount of data is collected to satisfy the requisite diagnostic needs. When an organ exhibiting a cyclical motion is studied, however, each cycle of the organ's motion must be separated into a finite number of segments and corresponding segments from a plurality of data cycles added (typically by a digital computer) so that each segment of a composite cycle has sufficient data to reproduce the organ in motion.

In cardiac imaging, the heart cycle is typically broken into, for example, 16 equally spaced intervals of time with the data representative of each of said intervals directed to selected locations within an imaging memory to help format the data for subsequent visual inspection and analysis. In a conventional cardiac study, the goal is to acquire sufficient data to reconstruct the various phases of the heart. This requires the inclusion of only that data which contributes to a regular heart cycle. However, the length of the heart cycle for a given patient, even at rest, may vary due to abnormalities in that patient, e.g., arrhythmia. Thus, a problem arises in the data collection since all of the heart beats in a given study may not lend themselves to an identical number of equally spaced intervals. Typically, the beginning of a cardiac cycle, for example as detected by an electrocardiogram (ECG), is used to trigger the start of a data acquisition cycle. Thus, if the heart beats at an irregular interval, the composite image formed by adding data from like numbered intervals of a series of cycles will be error filled. Some of the data will be missing as a result of restarting the data collection cycle before the system has completed the previous cycle. Other data will be included, but not synchronized, thereby adding further error to the final result.

There are two known approaches to radionuclide cardiac imaging. The first is to segment the cardiac cycle into a preselected number of equally spaced intervals and to start the data acquisition at the beginning of each cycle. The problem with this technique, as pointed out above, is that if the patient's heart beats prematurely during any cycle, the data collected in each interval during that cycle will be out of phase with the true cardiac data since the original interval calculation is based on the normal heart rate. The erroneous data cannot be removed from the study since they are already added into the cumulative data for each interval by the time the system can recognize that the cycle represents a shortened heartbeat. A similar problem occurs for each slow heartbeat.

The alternative is to collect all of the data generated by the camera system along with timing information that will permit the system to post-process the data acquired during the study and to reconstruct the heart in its various phases based only on the data collected in the heartbeats of interest. This is the technique currently used to overcome the limitations inherent in the variable heart rate; however, the technique obviously requires a great deal of on-line storage capability to contain all of the data and timing information. In addition, all of that data must be scanned and reformatted into the images of interest, adding delay to image formation.

DISCLOSURE OF THE INVENTION

I have invented a system for accurate and reliable real time cardiac data acquisition in which only data that meets a preselected heart rate is saved. Any data collected in a cardiac cycle that falls outside the desired heart rate is rejected and not included in the final results. This technique results in a significant savings in on-line storage requirements and avoids any post-processing required to view the final resulting images.

In accordance with the invention, a cardiac study is initiated in conventional fashion by administering the patient with a cardiac specific radionuclide, connecting the patient to an electrocardiograph, and monitoring the patient's ECG. In unconventional fashion, however, the image memory of the associated computer, is separated into at least three segments. The invention also comprises a disk subsystem that is part of a nuclear medicine computer subsystem with specialized interfacing connected to the image memory. Data acquisition is controlled such that only data from heart beats of approximately the same length are saved. A disk is used as a buffering device to acquire the end results of the study into the imaging memory. The specialized interfaced hardware in the disk subsystem provides the two methods of accessing the disk data that are required in this process. These two functions are the ability to write the data from a segment of image memory to the disk and concurrently clear the data from that segment of imaging memory, and the ability to read the data from the disk into another segment of imaging memory and to add that data to any data already contained in that segment of imaging memory. The size of the imaging memory required is at least three times the size of the storage required to hold the end result.

DETAILED DESCRIPTION OF THE PREFERRED EMBODIMENTS

The attached drawings show, in schematic form, preferred embodiments of a system and technique for real time cardiac radionuclide imaging using a disk subsystem. It is to be noted that, depending upon the predilection of the designer, the availability of specified parts, and the general technical capacity of the designer, the principles of the present invention may be employed to advantage both in a microprocessor based computational system, or in terms of more traditional hard wired logic. The schematic representations set forth in the attached drawings are believed sufficient to be readily understood and applied by those of ordinary skill either in the hard wired logic or the software and microprocessor arts to make and use the invention.

Figure 1:
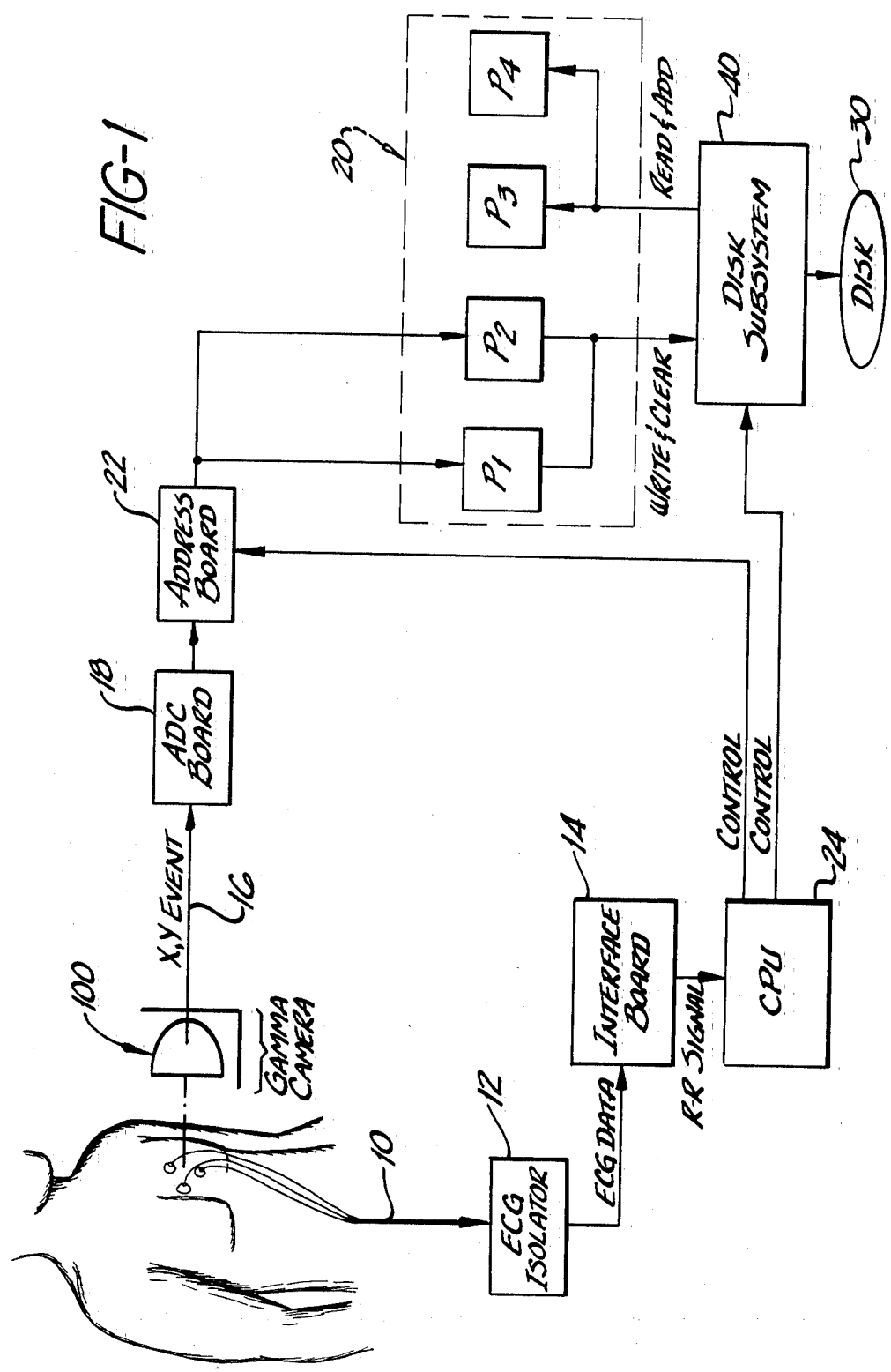
FIG. 1 is a functional block diagram of a nuclear camera system illustrating data flow in accordance with the present invention.

Referring first to a microprocessor based system, FIG. 1 serves to conceptually illustrate the data flow in such a system. A patient is connected to a nuclear camera computer system with a set of ECG leads 10 for collecting the time-variant voltages produced by the myocardium during the cardiac cycle.

Figure 4:
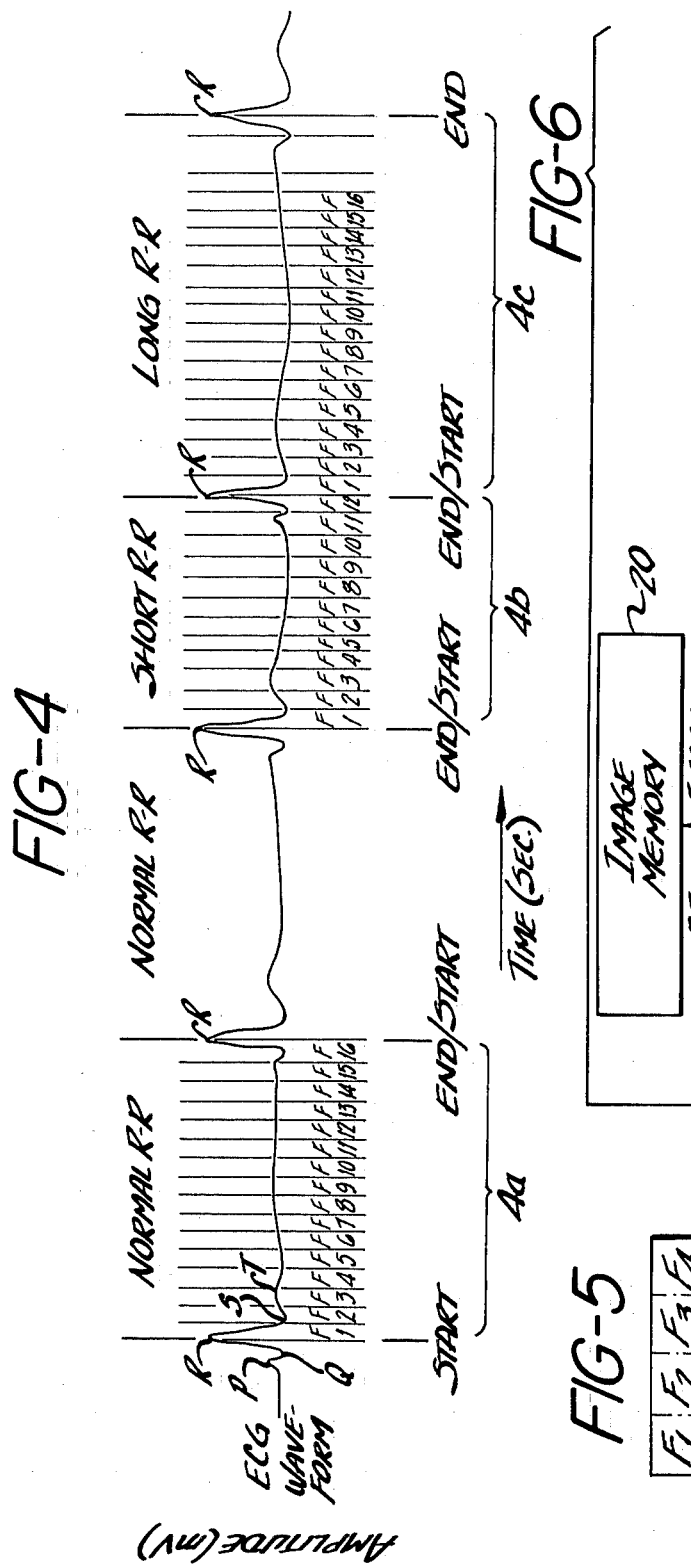
FIG. 4 is an electrocardiogram showing normal and abnormal durations.

By way of reference, FIG. 4 shows the basic waveform of the electrocardiogram. The P, QRS, and T waves reflect the rhythmic electric depolarization and repolarization of the myocardium associated with the contractions of the atria and ventricles. FIG. 4 illustrates a normal heart rate as measured by the R-R interval (FIG. 4a) as well as short (FIG. 4b) and long (FIG. 4c) cardiac cycles.

Referring again to FIG. 1, the signals transmitted by ECG leads 10 are coupled to a patient-isolating amplifier such as ECG ISOLATOR 12 before being routed to an interface circuit board designated INTERFACE BOARD 14. At the same time, gamma camera 100 collects the radioactivity from the heart of the patient in the form of gamma radiation emitted by a previously administered radionuclide. Gamma camera 100 includes a detector and an associated linear amplifier which translate each detected event into an X and Y analog position signal along with an analog signal indicative of the occurrence of a detected event. These analog signals are transmitted along line 16 and converted to a digital representation by an analog-to-digital (ADC) converter by ADC BOARD 18. The ADC BOARD 18 is in data communicating relationship with IMAGE MEMORY 20 via ADDRESS BOARD 22 which in turn is under microprocessor control by a central processing unit such as a Motorola MC 6800 microprocessor designated CPU 24.

The IMAGE MEMORY 20 includes four segments, $P_1$, $P_2$, $P_3$, and $P_4$. The two segments designated $P_1$ and $P_2$ are used in alternating fashion to collect successive cycles or pages of cardiac data with the duration of each cycle corresponding to one complete R-R interval. The beginning of each new cycle is triggered by the R-R signal which is applied to the CPU 24 by the INTERFACE BOARD 14. The ECG data also sets the time interval for each acquisition. As each R-R interrupt signal is processed by the CPU 24, the appropriate image memory segment $P_1$ or $P_2$ is selected to receive one heart beat of camera events. As each page of data is collected, it is written to DISK 30 and the data is cleared from the IMAGE MEMORY 20. The write and clear functions are performed by DISK SUBSYSTEM 40. For those heart beats (cycles of data) that are acceptable, the data is read from the DISK 30 and added to the page of IMAGE MEMORY 20 in segment $P_3$. The read and add functions are also performed by the DISK SUBSYSTEM 40. Segment $P_4$ of IMAGE MEMORY 20 is provided to permit the simultaneous accumulation of two sets of data as may be required, for example, when a particular study calls for the acceptance of two separate cardiac intervals. Additional segments of image memory $P_5 \ldots P_n$ can be added as required in order to collect additional cardiac intervals.

Figure 6:
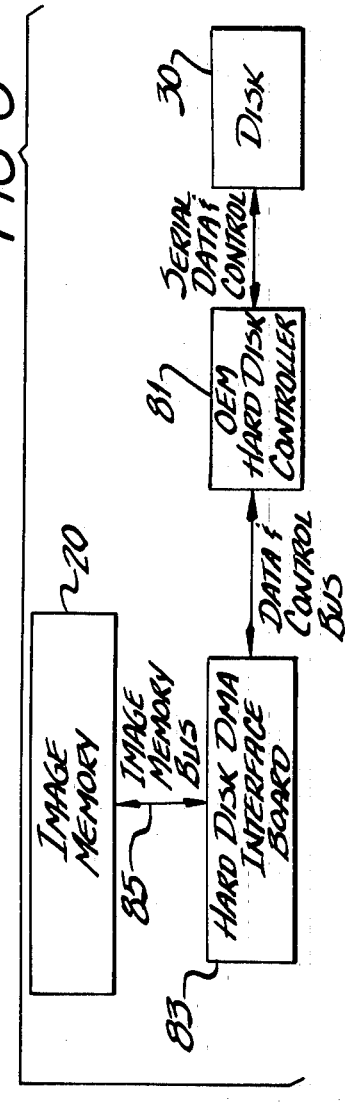
FIG. 6 is a functional block diagram of several of the disk subsystem components.
Figure 5:
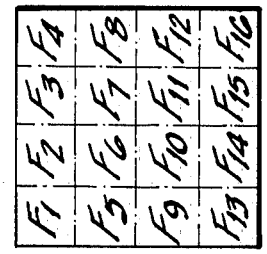
FIG. 5 is a diagrammatic illustration of a standard format of image memory related to data collection.
Figure 7:
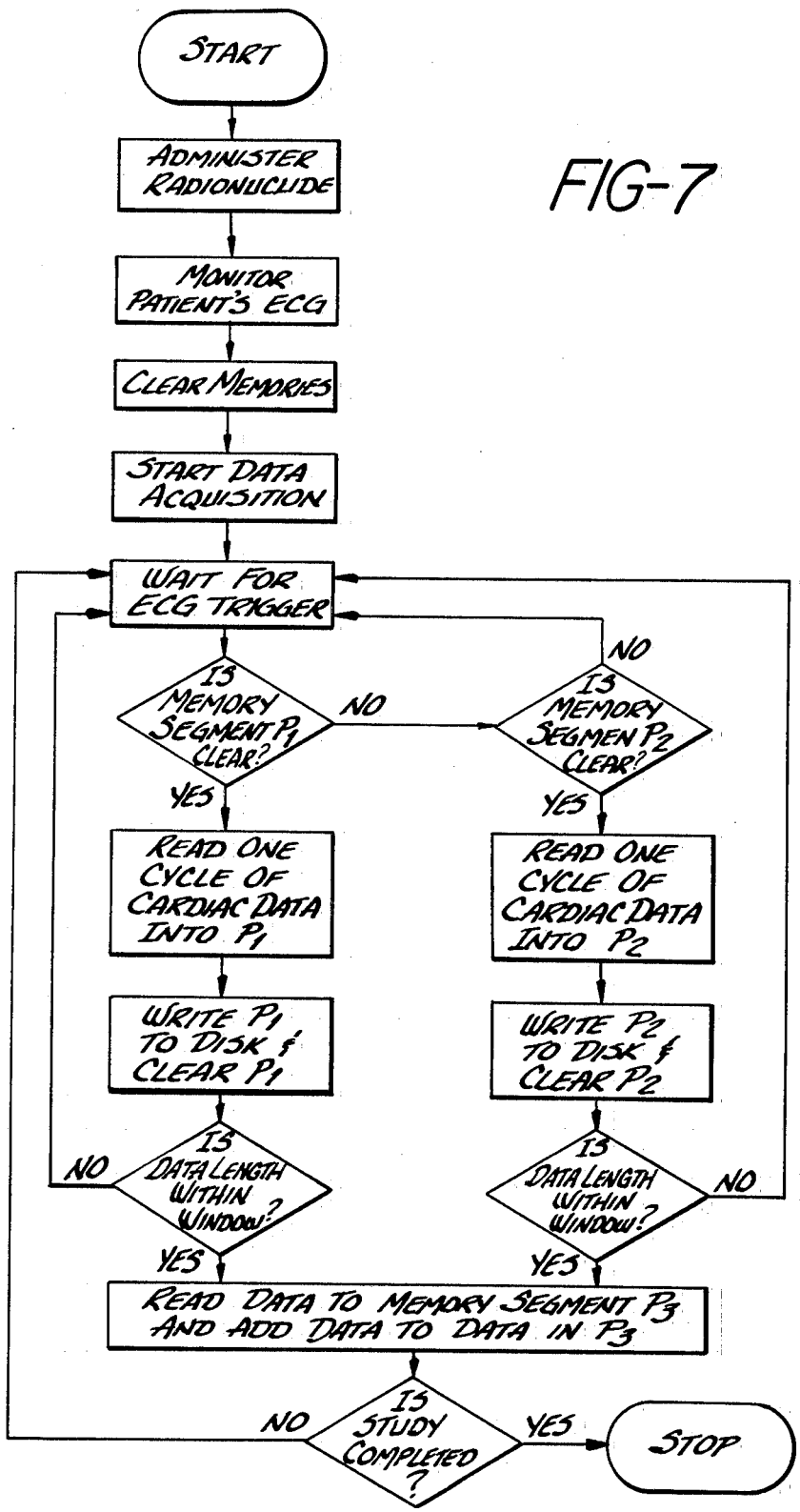
FIG. 7 is a flowchart of a method for real time cardiac imaging in accordance with the present invention.

The operation of the system depicted in FIG. 1 is delineated in the flowchart presented in FIG. 7. The preparatory steps of administering a radionuclide and connecting the patient to an ECG are performed. Also, the appropriate storage sections of the computer's memory are cleared. Once data acquisition is started, a cycle of data is initiated by the R-R trigger signal with the ADDRESS BOARD 22 determining into which memory segment the cycle of data is read. If segment $P_1$ is clear, then one cycle of cardiac data is acquired in $P_1$. As shown in FIG. 4, each cycle or page of data is segmented into a plurality of frames ($F_1 \ldots F_n$) each representing data collected from the heart during $1/n$ of a cycle. Each frame of data is formatted in memory as shown in FIG. 5. After the cycle of data acquired in $P_1$ is completed as signaled by a new R-R signal, the cycle of data is written to DISK 30 and the contents of $P_1$ cleared. This write and clear function is performed by DISK SUBSYSTEM 40 whose components are shown in FIG. 6 and described in greater detail below.

The data read to DISK 30 from $P_1$ is examined to determine whether its cycle length falls within a prescribed window, i.e., a permissible time range. If the data satisfies this window test, then it is read to memory segment $P_3$ where it is added to the previous contents of $P_3$. Memory segment $P_3$ is also formatted such as shown in FIG. 5 so that like numbered segments (F1 through F16) from the numerous cycles constituting a single cardiac study are separately accumulated. This read and add function is also performed by DISK SUBSYSTEM 40. Alternatively, if the data in DISK 30 does not fall within the preselected window, the system cycles back to the block designated WAIT FOR ECG TRIGGER, and the data from the unaccepted cycle are deleted without affect on cumulative final images. As the contents of $P_1$ are written to DISK 30, the next cardiac cycle is acquired in memory segment $P_2$. In like fashion, when the acquisition of data in $P_2$ is completed as signaled by the next R-R signal, the contents of $P_2$ are written to DISK 30 and segment $P_2$ is cleared. Again a determination is made regarding the length of the cycle of data written to DISK 30. If the length falls within the prescribed window, then the contents of DISK 30 are written to memory segment $P_3$ and added to the data already in $P_3$. The process continues until the study is completed. Depending upon the type of study, it may be completed as a function of time, a predetermined number of heart beats, or when the data count reaches a prescribed minimum threshold. The technique is sufficiently flexible to permit the collection of data based not only on just one cardiac interval but a series of sets of images with each set representing a specific interval range. This is accomplished by designating a larger address array on the DISK 30 for use as a scratch pad and segmenting the space into separate image groupings. Each group of images represents a particular heart rate interval (e.g., 50 milliseconds difference per group). According to this variation, a single cardiac cycle is collected in the IMAGE MEMORY 20. After a cardiac cycle acquisition is completed, its length is computed and compared to the various available interval locations. Once the interval location on the DISK 30 is identified, its contents are read and added to the segment of IMAGE MEMORY 20 in which the cardiac cycle data was acquired. Then, the summed data is written back into the DISK 30 at the selected interval and the contents of the image memory is cleared. The DISK 30 contains a set of cardiac cycles ranging from, for example, 700 milliseconds to 1000 milliseconds in, for example, 50 millisecond increments. The data accumulated at each location represents a set of cumulative images of the heart beat corresponding to the interval length (i.e., all the cardiac cycles in the range of 700 to 750 milliseconds would be in one group, all the cardiac cycles in the range of 750 to 800 milliseconds would be in another group, and so on). After sufficient data is accumulated in the intervals of interest, any interval is easily read from the DISK 30 to the IMAGE MEMORY 20 and then transferred to a video monitor (not shown) in conventional fashion. This process affords the clinician the ability to simultaneously record data representing a series of cardiac cycle intervals and thus, to perform more exhaustive analysis techniques on the collected data.

FIG. 6 shows the components of the DISK SUBSYSTEM 40 in data communicating relationship with IMAGE MEMORY 20. The DISK SUBSYSTEM 40 connects to DISK 30 which is preferably a Winchester type hard disk drive such as the Shugart SA 4008 which is in data communicating relationship with a disk controller designated OEM HARD DISK CONTROLLER 81. The disk controller may be purchased from Data Management Laboratories. The DISK SUBSYSTEM 40 also includes an interface circuit board designated HARD DISK DMA INTERFACE BOARD 83. The purpose of board 83 to interface between the IMAGE MEMORY BUS 85 which has data from the gamma camera 100 and the HARD DISK CONTROLLER 81 in order to transfer data from the DISK 30 to IMAGE MEMORY 20 and back.

Figure 2:
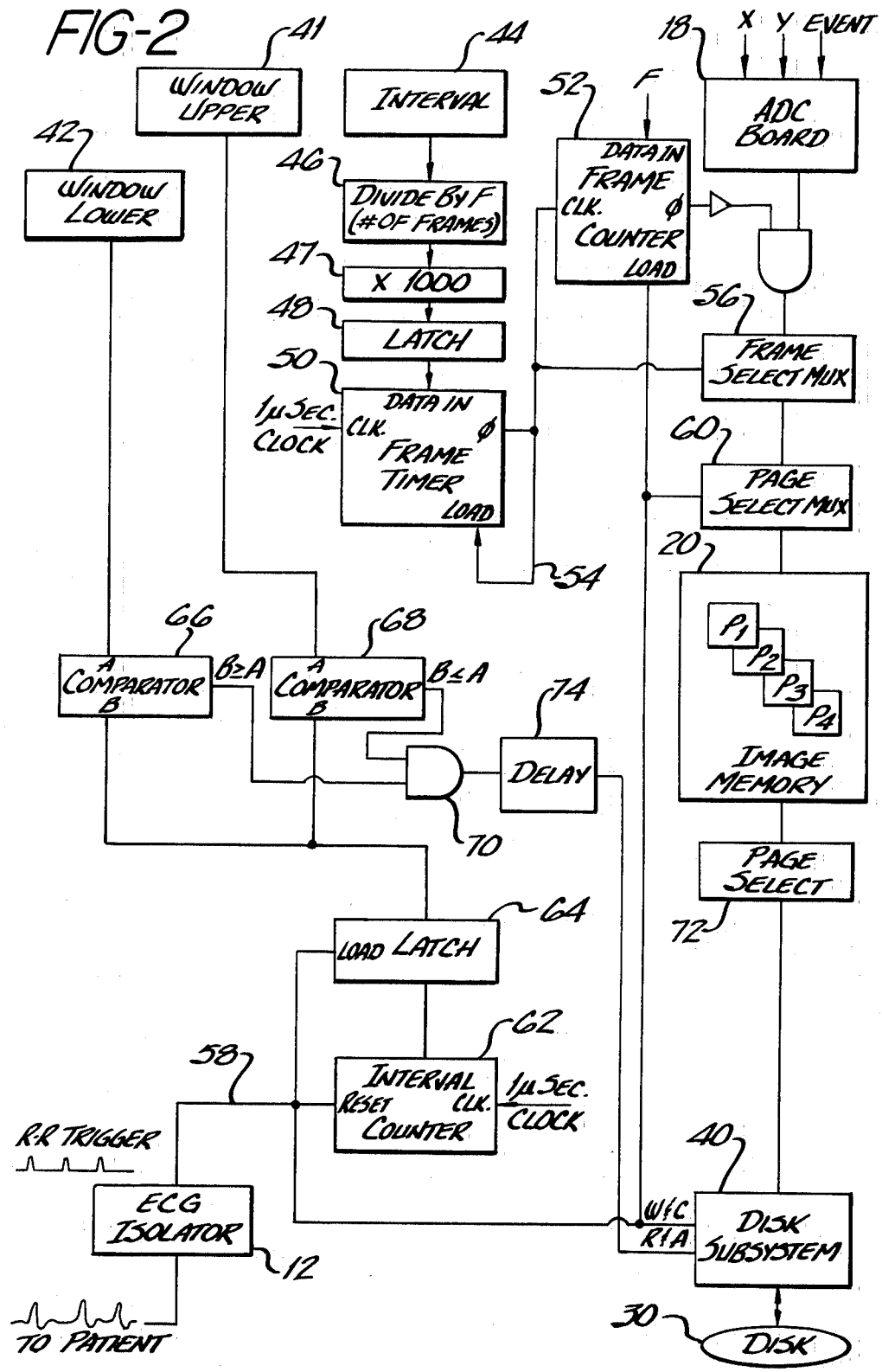
FIG. 2 is a functional block diagram illustrating a hardware implementation of the present invention.

A hard wired logic implementation of a preferred embodiment of the present invention is presented in block diagram form in FIG. 2. An acceptable time frame for cardiac intervals is established by a pair of switches such as WINDOW UPPER 41 and WINDOW LOWER 42 which are used to select the upper and lower interval range, respectively, for selection of the acceptable cycles of cardiac data. A separate switch, such as INTERVAL 44 is used to select the normal interval that is to be accepted. At the beginning of each study, the user sets the window and time interval by setting the switches 40, 42 and 44 before initiating the study. All of the selections are conveniently expressed in milliseconds. The value selected at INTERVAL 44 is divided down by the number of frames F to be acquired for each cycle at DIVIDE BY F 46, rescaled at block 47 designated X 1000, and latched by LATCH 48 into a down counter such as FRAME TIMER 50. FRAME TIMER 50 is driven by a signal from a one microsecond clock, hence the need for the three order of magnitude conversion. When the down counter 50 reaches 0 it is reset and transmits a signal to a multiplexer such as FRAME SELECT MUX 56. Multiplexer 56 serves to steer the EVENT signals received from the ADC BOARD 18 into the individual frames of data on each page of image memory. As the counter 50 reaches 0, a second counter such as FRAME COUNTER 52 is clocked. FRAME COUNTER 52 serves to count the number of frames collected for each cardiac cycle by counting from F to 0 in order to stop the frame advance when sufficient data has been collected and the R-R interval is longer than the normal interval. When the FRAME COUNTER 52 reaches 0, data collection stops until the next R-R interval is started.

The ECG ISOLATOR 12 serves to generate a trigger signal (R-R TRIGGER) along line 58 at the peak of each cardiac cycle. The trigger signal on line 58 serves a multitude of functions. One of its functions is to control a multiplexer such as PAGE SELECT MUX 60 to select between image memory segment $P_1$ and $P_2$. This selection determines in which segment the current cardiac cycle data is acquired in the IMAGE MEMORY 20. The R-R TRIGGER signal also serves to reset INTERVAL COUNTER 62 which counts in milliseconds the duration that has elapsed from the previous trigger signal. The cumulative value in the INTERVAL COUNTER at the time it is reset is loaded into LATCH 64 for subsequent comparison by each of two COMPARATORS 66 and 68. COMPARATOR 66 compares the duration value stored in LATCH 64 with the selected value in WINDOW LOWER 42. If the comparison results in the LATCH value being greater than or equal to the WINDOW LOWER value, than the COMPARATOR 66 outputs a logical 1, but if the converse is true than the output is a logical 0. The output of COMPARATOR 66 is applied to one of the inputs of AND gate 70. Similarly, the value stored in LATCH 64 is compared to the preselected value in WINDOW UPPER 41 by COMPARATOR 68. If the LATCH value is less than or equal to the WINDOW UPPER value, than COMPARATOR 68 outputs a logical 1, but if the converse is true, the output of COMPARATOR 68 is a logical 0. The output of COMPARATOR 68 is applied to the other input of AND gate 70. The AND gate 70 senses the outputs from the two COMPARATORS 66 and 68 and issues a logical 1 at its output whenever both of its inputs are logical 1s. A logical 1 will issue from AND gate 70 whenever the latest interval is within the LOWER and UPPER WINDOW values. If the comparison is such that the interval is acceptable, then a read and add (R&A) signal is applied to the DISK SUBSYSTEM 40 which causes the contents of DISK 30 to be written and added to a segment of image memory, such as $P_3$ or $P_4$. This routing decision is made by another multiplexer such as PAGE SELECT 72. The R&A signal is delayed by DELAY 74 so that the read and add transfer is not performed until after any previous write and clear (W&C) transfer is completed. If the comparisons show an unacceptable value, i.e., when the output of AND gate 70 is a logical 0, then no R&A signal is applied to the DISK SUBSYSTEM 40, resulting in the data in the DISK 30 being overwritten by the next write cycle. The final effect of the R-R signal is to initiate a write and clear (W&C) cycle for writing to the DISK 30 from a page of IMAGE MEMORY 20 the previously accumulated cardiac cycle data and to clear that page (i.e., $P_1$ or $P_2$) of IMAGE MEMORY 20.

Figure 3:
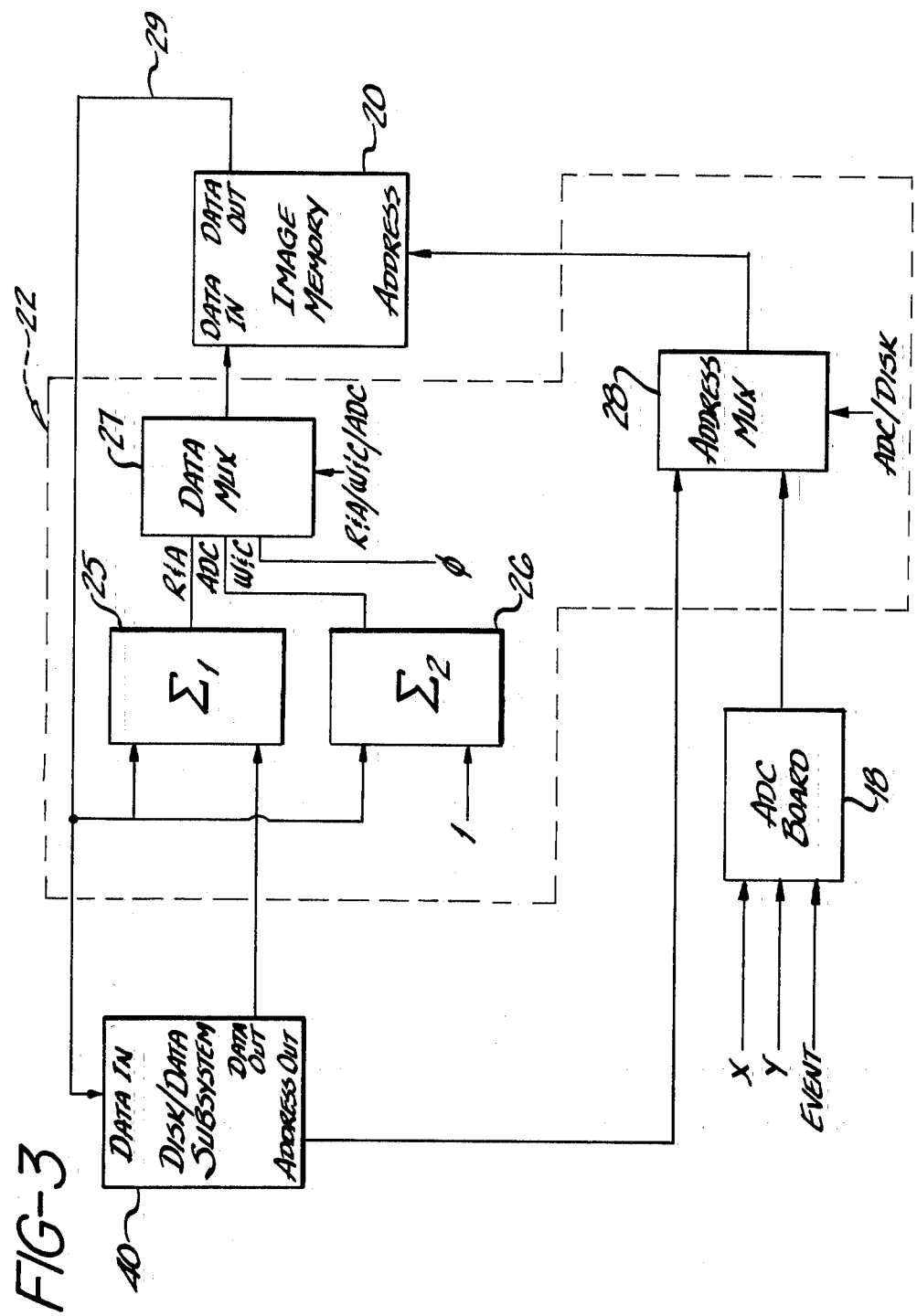
FIG. 3 illustrates a disk subsystem interface to the image memory in accordance with the present invention.

The disk subsystem interface to the IMAGE MEMORY 20 of the computer system is diagrammed in FIG. 3. This diagram shows how the data to and from the DISK 30 via the DISK SUBSYSTEM 40 is routed into and out of the IMAGE MEMORY 20. ADDRESS BOARD 22 is shown in greater detail as comprising two adders ($\Sigma_1$ and $\Sigma_2$) identified as block 25 and 26, respectively, and two multiplexers such as DATA MUX 27 and ADDRESS MUX 28, respectively. ADDRESS MUX 28 selects either data coming from the A to D converters on the ADC BOARD 18 or data coming from the DISK 30. ADDRESS MUX 28 controls the address selection of the data being routed to the IMAGE MEMORY 20 from the DISK 30 or ADC BOARD 18. The DATA MUX 27 controls which data is being placed in the DATA IN input of IMAGE MEMORY 20. Multiplexer 27 can input data into the IMAGE MEMORY 20 either from the DISK 30, from the ADC BOARD 18, or data coming from a zero connection for the clearing function. If the DATA MUX 27 chooses data from the DISK 30 then it will perform a read and add function, taking the data from the DISK and adding it to data already in a page of image memory through adder 25. If data is coming directly from the analog-to-digital converters of the ADC BOARD 18, then it will perform an add of 1 by adder 26 to the data point in IMAGE MEMORY 20 selected by ADC BOARD 18 and ADDRESS MUX 28.

There is also provided a feedback loop 29 between the DATA OUT output of IMAGE MEMORY 20 and one of the inputs of each of the adders 25 and 26. Adder 25 is used to add the data in the image memory from the data being read from the DISK 30. Adder 26 is used to count each event from ADC BOARD 18 by incrementing by 1 the selected point in the IMAGE MEMORY 20 as selected by ADDRESS MUX 28.

Although the invention has been described in connection with cardiac imaging, it will be apparent to those skilled in the art that the technique has application in the imaging of any periodically moving object requiring only that the relevant rhythmic motion be monitored.

I claim:

1. A data acquisition system for use in radionuclide cardiac imaging of a patient having been administered a myocardium specific radionuclide, comprising:
   (a) means for monitoring the electrical activity of the heart;
   (b) first temporary storage means for accumulating respective pages of data corresponding to nuclear events during each said cardiac cycle;
   (c) means, responsive to said means for monitoring, for determining the time duration of each successive cadiac cycle;
   (d) means for comparing each said determined duration of a cardiac cycle with a preselected time duration range;
   (e) second temporary storage means; and
   (f) means for conditionally transferring pages of data from said first temporary storage means to said second temporary storage means if the measured duration associated with each said page has predetermined correspondence with said preselected duration range, whereby pages of data having said predetermined correspondence may be collated into a quasi-real time study, while pages of data having different correspondence with said preselected time duration range are discarded form said study.

2. A data acquisition system as described in claim 1 wherein said first temporary storage means comprises a disc memory means, pages of data having said predetermined correspondence being transferred from said disc memory means to said second temporary storage means, and pages of data not having said predetermined correspondence being deleted from said disc memory means.

3. A data acquisition system as described in claim 2 and further including buffer memory means which includes two separate portions, each being alternatively utilized to accumulate pages of data corresponding to nuclear events during given successive cardiac cycles, a page of data from one portion being transferred to said disc memory means while a page of data from a next subsequent cycle is being accumulated in an alternative portion of said buffer memory means.

4. A data acquisition system as described in claim 3 wherein said buffer memory means and said second temporary storage means comprises respective portions of a single memory means, divided appropriately into segments for performing the respective functions of each.

* * * * *